(12) United States Patent
Liu

(10) Patent No.: US 7,775,997 B2
(45) Date of Patent: Aug. 17, 2010

(54) NON-ELECTRICAL DRIVEN DENTAL HYGIENE PULSATING SPRAYER

(76) Inventor: Michael C. Liu, No. 282, Hsiang Yang Rd., Feng Yuan City, Taichung Hsien (TW)

( * ) Notice: Subject to any disclaimer, the term of this patent is extended or adjusted under 35 U.S.C. 154(b) by 1106 days.

(21) Appl. No.: 11/448,541

(22) Filed: Jun. 7, 2006

(65) Prior Publication Data

US 2006/0229537 A1    Oct. 12, 2006

Related U.S. Application Data

(63) Continuation-in-part of application No. 10/696,157, filed on Oct. 29, 2003, now abandoned.

(51) Int. Cl.
*A61H 9/00* (2006.01)
*A61H 13/00* (2006.01)

(52) U.S. Cl. .................... 601/162; 601/165

(58) Field of Classification Search .............. 601/154, 601/155, 160, 161, 162, 163, 165, 169; 433/80, 433/82, 88

See application file for complete search history.

(56) References Cited

U.S. PATENT DOCUMENTS

| 4,190,207 A |   | 2/1980  | Fienhold et al. |
|-------------|---|---------|-----------------|
| 4,257,433 A | * | 3/1981  | Kwan .................. 601/162 |
| 4,629,125 A |   | 12/1986 | Lin |
| 4,793,331 A |   | 12/1988 | Stewart |
| 5,070,864 A | * | 12/1991 | Lemons .................. 601/160 |
| 6,740,053 B2| * | 5/2004  | Kaplowitz .................. 601/162 |

* cited by examiner

*Primary Examiner*—Quang D Thanh
(74) *Attorney, Agent, or Firm*—Jackson Walker, LLP

(57) ABSTRACT

A dental hygiene pulsating sprayer has a handle and a pulsating engine having a turbine rotor. The handle is adapted to connect to a water source. The turbine rotor is rotatably received in the pulsating engine and has a curved wall, a top cover and multiple extension blades. The top cover is attached to the curved wall to construct a circle in cooperation with the curved wall. The extension blades are formed on and extend radically from the top cover and the outer periphery of the curved wall. Accordingly, the sprayer can provide a pulsating massage effect and is not driven by electrical power.

17 Claims, 16 Drawing Sheets

NON-ELECTRICAL DRIVEN DENTAL HYGIENE PULSATING SPRAYER

The present invention is a continuation-in-part of application Ser. No. 10/696,157 filed on Oct. 29, 2003 now abandoned.

BACKGROUND OF THE INVENTION

1. Field of Invention

The present invention relates to a sprayer, and more particularly to a dental hygiene pulsating sprayer that can provide a pulsating massage effect and is not driven by electrical power.

2. Description of the Related Art

To clean teeth, a toothbrush is always used with toothpaste. However, the conventional toothbrush is inconvenient in use, and the user, especially a child, cannot sufficiently clean teeth with a conventional toothbrush. Therefore, an oral irrigator is provided to spray water for cleaning teeth of a user. A conventional oral irrigator substantially comprises a handle with a head and a pump. The head is mounted on one end of the handle. The handle is connected at its other end to a water source through a hose. The pump is used to pump the water to spray out from the head of the handle, and the sprayed water can be used to efficiently clean teeth of a user.

However, the conventional oral irrigator needs electrical power to drive the pump to work, so a high cost is involved in using the conventional oral irrigator. That is, the special miniature motor required is costly, as are the batteries required to drive the motor.

To overcome the shortcomings, the present invention provides a dental hygiene sprayer functioning as a plumbing fixture or as a portable device to mitigate or obviate the aforementioned.

SUMMARY OF THE INVENTION

The main objective of the invention is to provide a dental hygiene pulsating sprayer that can provide a pulsating massage effect and is not driven by electrical power. The dental hygiene pulsating sprayer has a handle and a pulsating engine having a turbine rotor. The handle is adapted to connect to a water source. The turbine rotor is rotatably received in the pulsating engine and has a curved wall, a top cover and multiple extension blades. The top cover is attached to the curved wall to construct a circle to in cooperation with the curved wall. The extension blades are formed on and extend radically from the top cover and the outer periphery of the curved wall. Accordingly, the turbine rotor can be driven to rotate when water impacts on the extension blades of the turbine rotor, and the water stream will be interrupted by the turbine rotor. Consequently, a pulsating water stream is generated, and a pulsating massage effect is provided.

Other objectives, advantages and novel features of the invention will become more apparent from the following detailed description when taken in conjunction with the accompanying drawings.

DETAILED DESCRIPTION OF THE INVENTION

Figure 1:
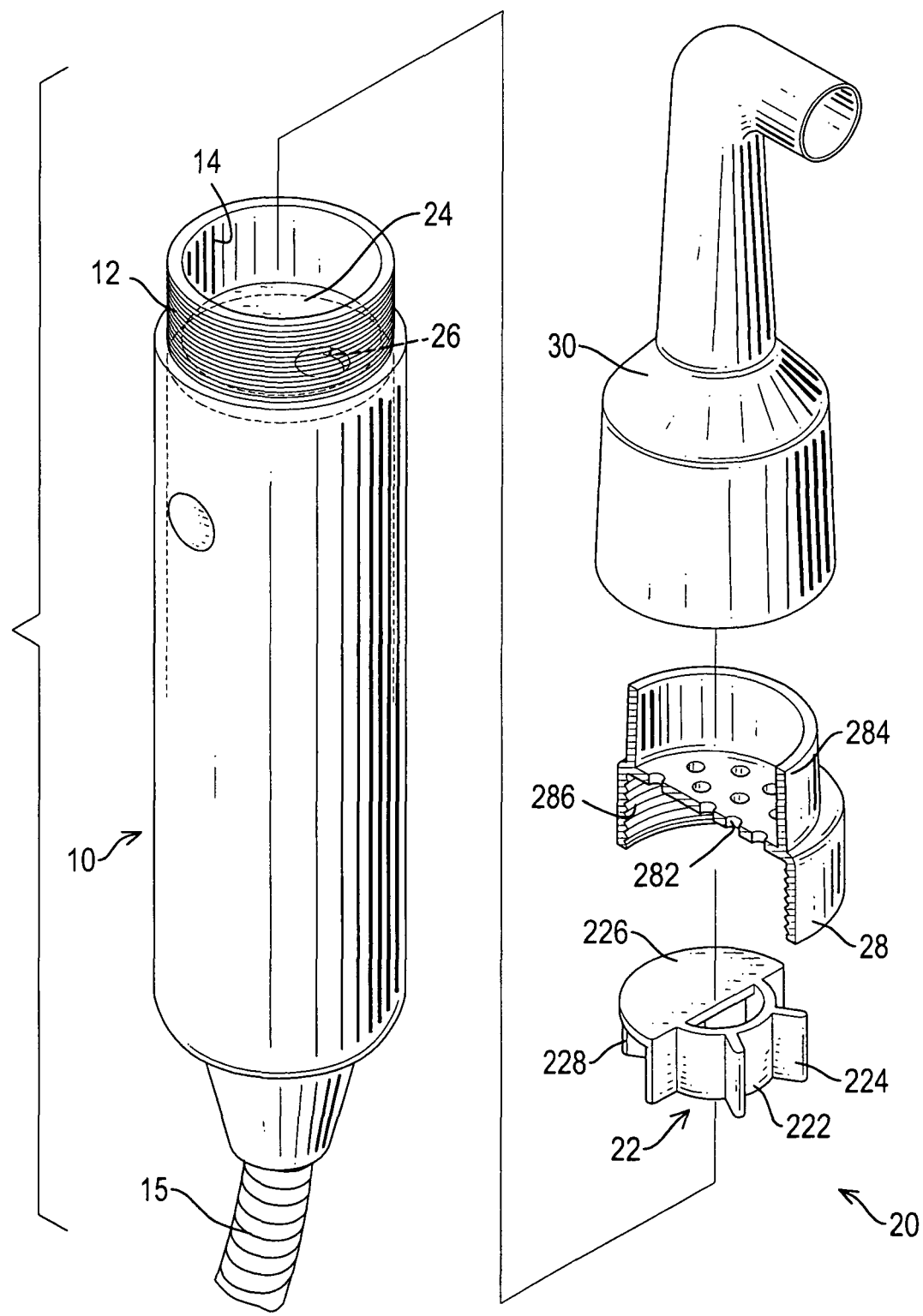
FIG. 1 is an exploded perspective view of a first embodiment of a dental hygiene sprayer in accordance with the present invention.
Figure 2:
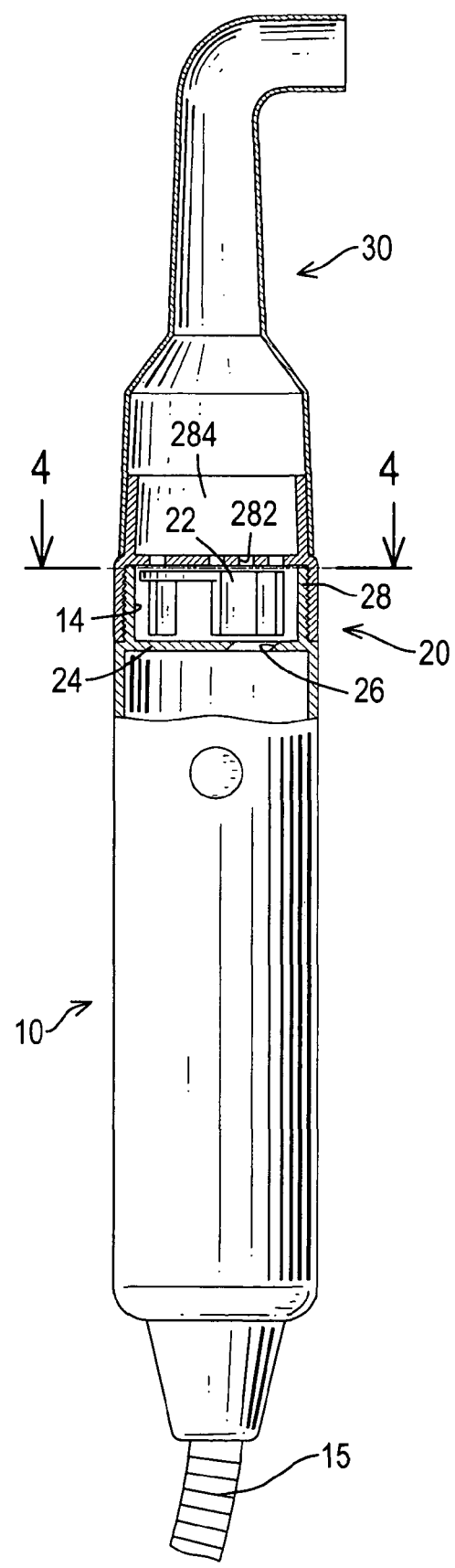
FIG. 2 is a side plan view in partial cross section of the first embodiment of the sprayer in FIG. 1.

With references to FIGS. 1 and 2, in a first embodiment of a dental hygiene pulsating sprayer in accordance with the present invention comprises a handle (10), a pulsating engine (20) and a spraying head (30). The handle (10) has an inlet end, an outlet end, a first passage and an outer thread (12). The first passage extends through the handle (10) from the inlet end to the outlet end. The outer thread (12) is formed on the outlet end. The inlet end is connected to a water source through a hose (15).

Figure 3:
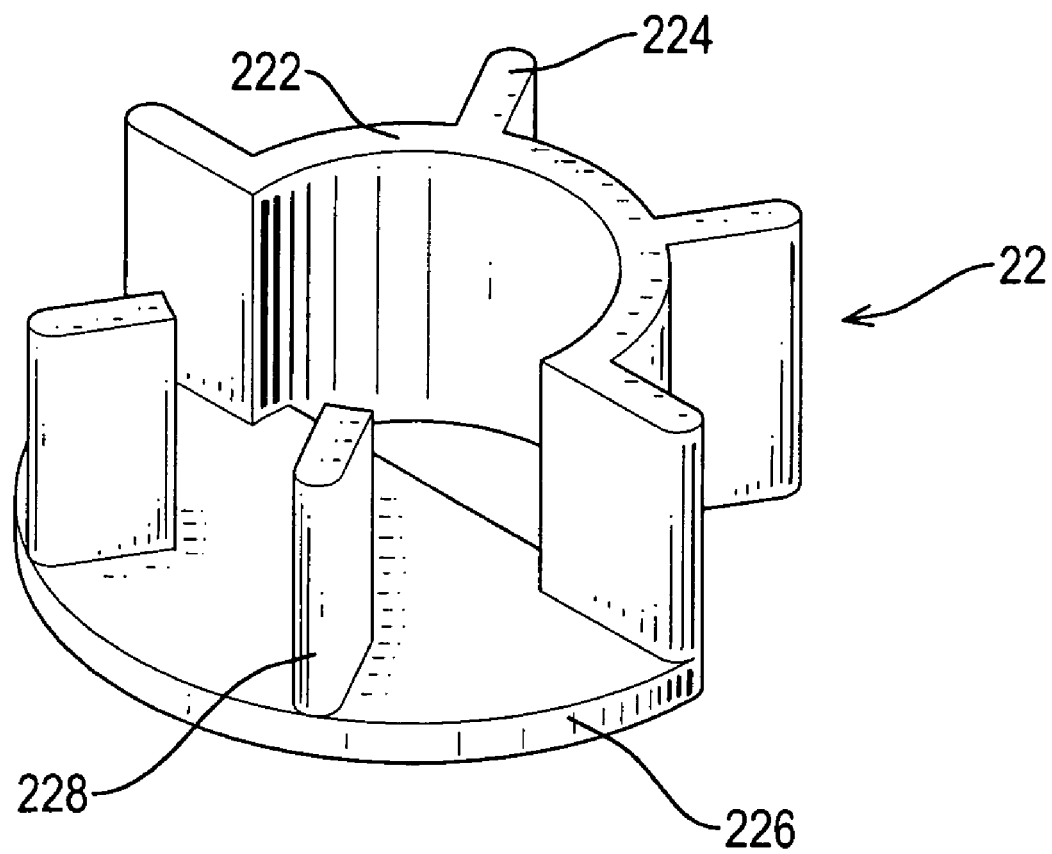
FIG. 3 is a bottom perspective view of the turbine rotor of the sprayer in FIG. 1.

The pulsating engine (20) is connected to the outlet end of the handle (10) and has a turbine rotor (22), a baffle (24), at least one inclined bore (26) and a cap (28). With further reference to FIG. 3, the turbine rotor (22) is rotatably received in the pulsating engine (20) and has a curved wall (222), multiple first extension blades (224), a top cover (226) and multiple second extension blades (228). The curved wall (222) has an outer periphery, and the first extension blades (224) are formed on and extend radially from the outer periphery of the curved wall (222). The top cover (226) is integrally formed with the curved wall (222) to construct a circle in cooperation with the curved wall (222). The second extension blades (228) are radially formed on the top cover (226) and correspond to the first extension blades (224) on the curved wall (222).

Figure 4:
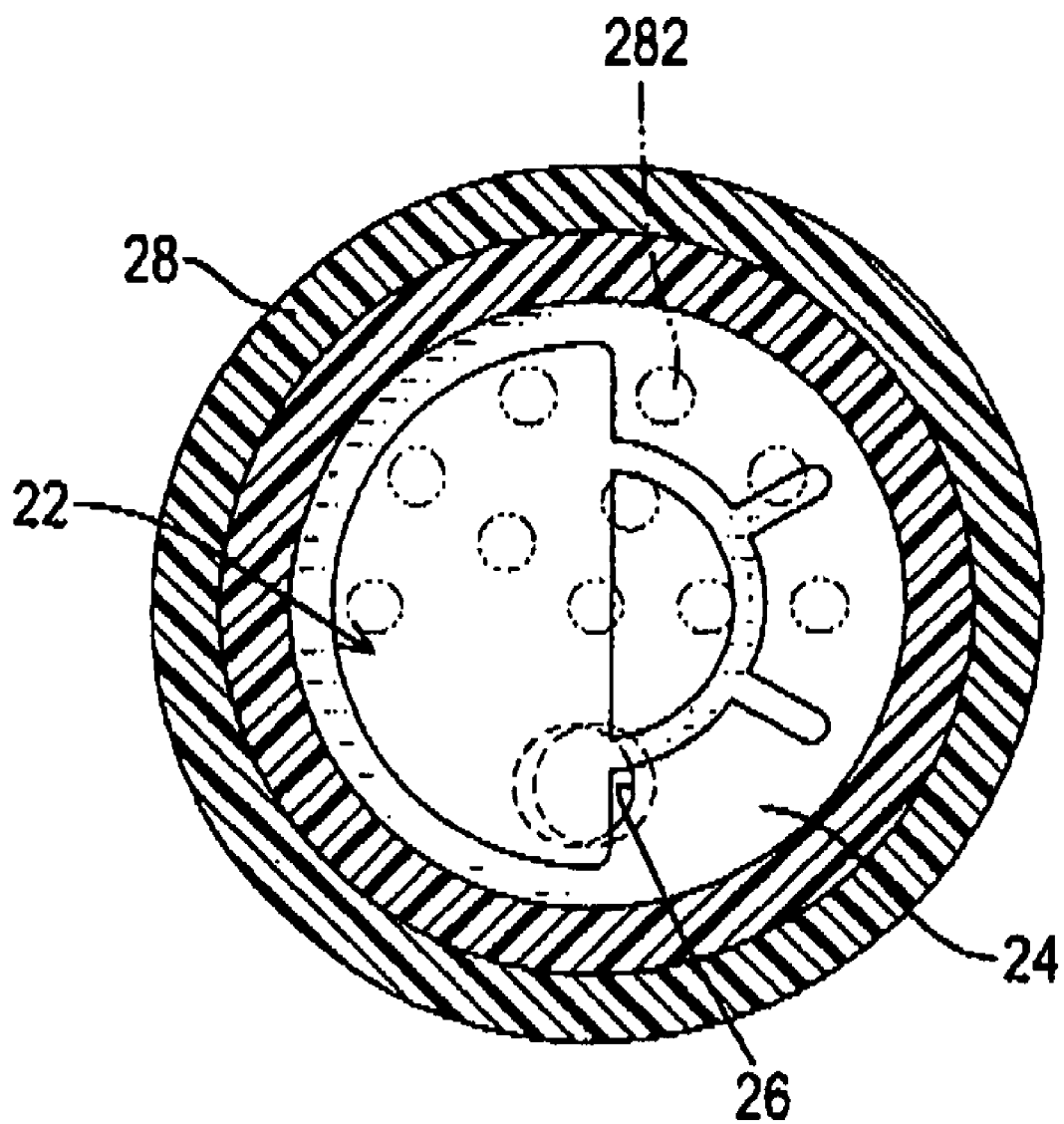
FIG. 4 is a cross sectional top plan view of the first embodiment of the sprayer along line 4-4 in FIG. 2.

With further reference to FIG. 4, the baffle (24) is formed at the entrance of the pulsating engine (20) near the outlet end of the handle (10) so as to define a chamber (14) in the outlet end of the handle (10). At least one inclined bore (26) is defined through the baffle (24) and communicates the chamber (14) with the first passage. The cap (28) is attached to the outlet end of the handle (10) to close the chamber (14). The cap (28)

has at least one through hole (282), a connecting tube (284) and an inner thread (286). The inner thread (286) is screwed with the outer thread (12) on the handle (10) to attach the cap (28) to the handle (10). The through holes (282) are defined through the cap (28) and communicate with the chamber (14). The connecting tube (284) extends from the cap (28) and encloses the through holes (282).

In a preferred embodiment, the through holes (282) are arranged in a half portion (50%) of the cap (28), and the top cover (226) has an area half of the whole circle (50%) constructed by the top cover (226) and the curved wall (22). To effectively generate a pulsating stream, the ratio of the top cover (226) to the circle constructed by the top cover (226) in cooperation with the curved wall (222) is equal to, or greater than the ratio of total distributed area of the through holes (282) to area of the cap (28). The through holes are arranged within a portion of the cap that is fully coverable by the top cover. Accordingly, the ratio of total distributed area of the through holes (282) to the whole area of the cap (28) can be further adjusted to perform different patterns of pulsating stream. In addition, when total occupied area of the through holes (282) increases, the turbine rotor (22) will rotate more slowly so as to reduce the pulsating frequency of water stream. Accordingly, manipulation of total occupied area of the through holes (282) can adjust the pulsating frequency of water stream.

The spraying head (30) is attached to the cap (28) of the pulsating engine (20). The spraying head (30) is L-shaped and has a proximal end, a distal end and a second passage. The second passage is defined through the spraying head (30) from the proximal end to the distal end. The proximal end is mounted onto the connecting tube (284) on the cap (28) to attach the spraying head (30) to the cap (28), such that the second passage in the spraying head (30) communicates with the pulsating engine (20).

Figure 5:
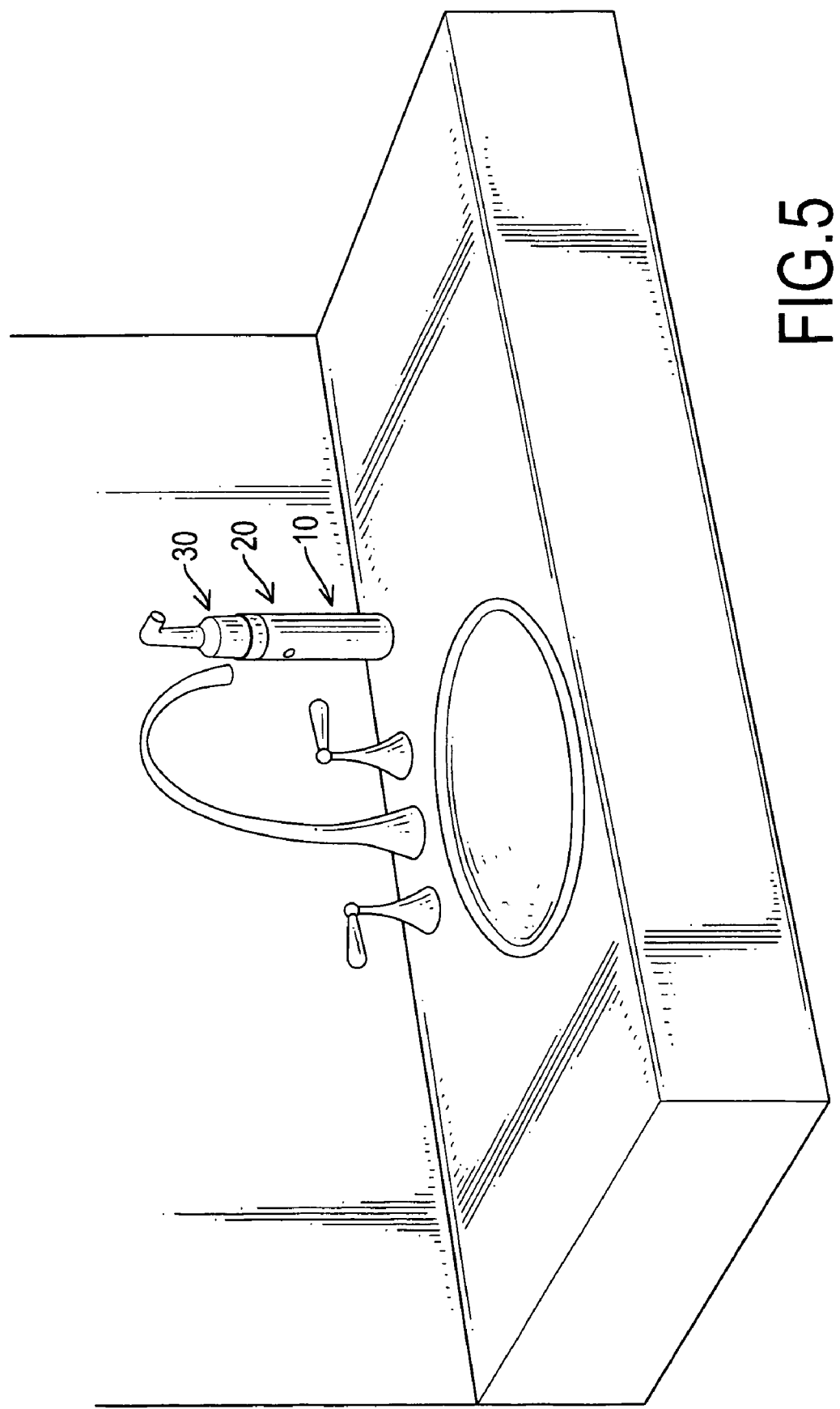
FIG. 5 is a perspective view of a washbasin with a sprayer in FIG. 1.
Figure 6:
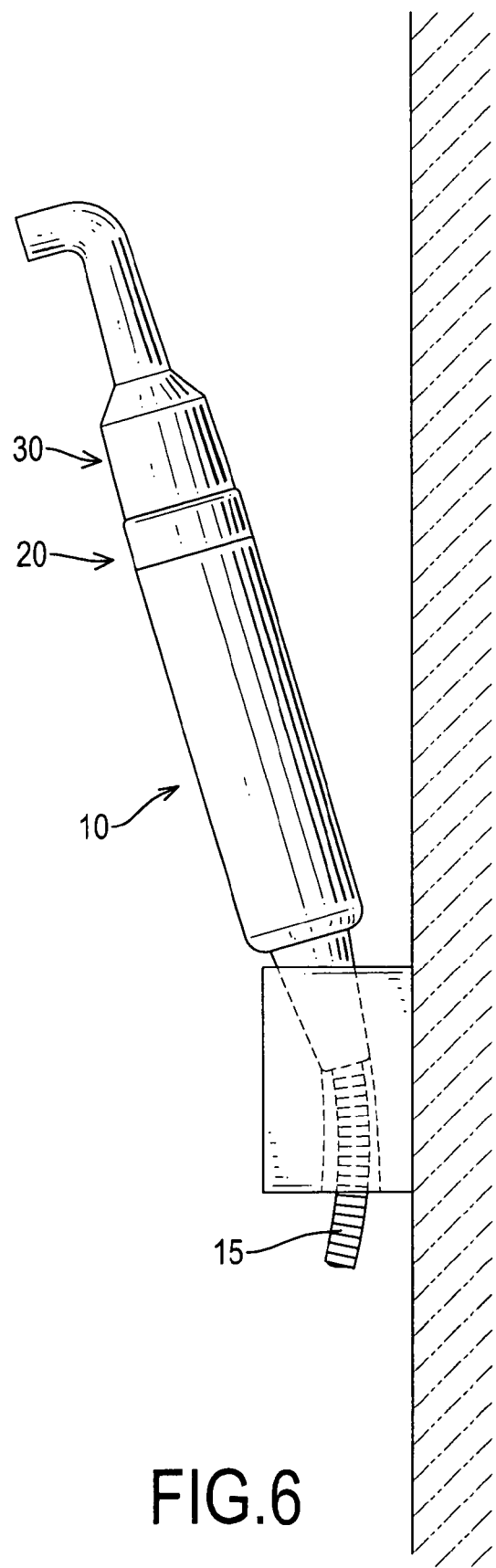
FIG. 6 is an operational side plan view of the sprayer in FIG. 1 showing that the sprayer is hung on a wall.

With further reference to FIGS. 5 and 6, the sprayer is connected to a water tap through the hose (15) and can be mounted on a washbasin or attached on a wall as a spray head operating in a shower area. When a user turns on the water tap, the water will flow into the first passage in the handle (10) through the hose (15) and flow into the chamber (14) through at least one inclined bore (26). Water will spray out from the spraying head (30) through the through holes (282) in the cap (28) and the second passage in the spraying head (30) for cleaning teeth of the user. When water passes through the inclined bore (26), the inclined bore (26) makes water impact on the blades of the turbine rotor (22) so as to rotate the turbine rotor (22) in the chamber (14). Accordingly, the water stream passing through the chamber (14) will be interrupted by the top cover (226) when the turbine rotor (22) rotates, such that a pulsating stream is generated. Consequently, the discharged water from the spraying head (30) can provide a pulsating massage effect to the gum of the user when the user cleans teeth with the sprayer.

Because the sprayer is connected to a water system in a house and the turbine rotor (22) is driven by the water pressure, electrical power is not needed for the operation of the sprayer. To use the pulsating sprayer is convenient, safe and involves a low cost.

Figure 7:
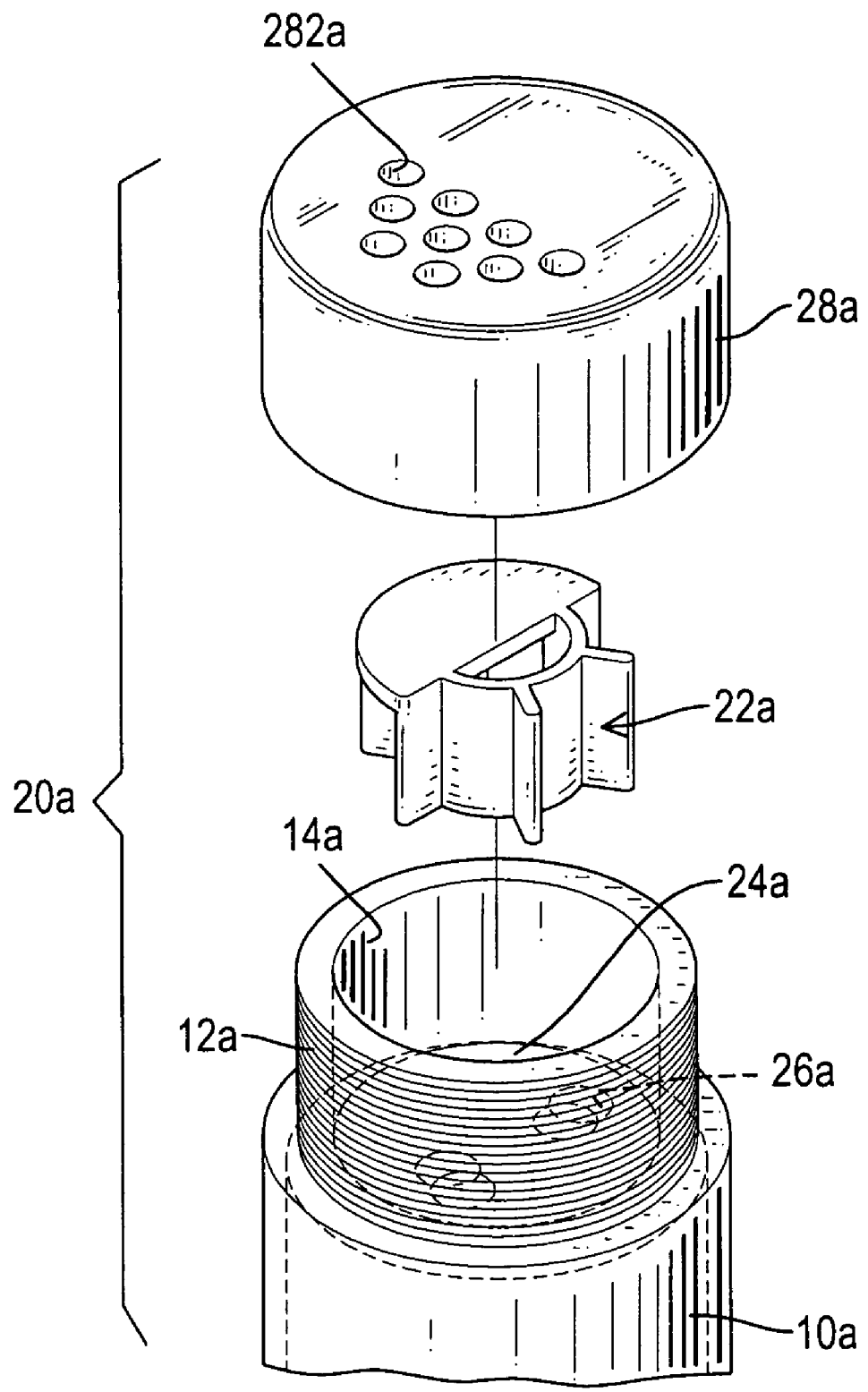
FIG. 7 is a perspective view of a pulsating engine of a second embodiment of a dental hygiene sprayer in accordance with the present invention.

With reference to FIG. 7, in a second embodiment of a sprayer in accordance with the present invention, the sprayer comprises a handle (10a) and a pulsating engine (20a). The handle (10a) has an outlet end, an inlet end and a first passage and is connected to a water source through a hose. The pulsating engine (20a) is connected to the outlet end of the handle (10a) and has a turbine rotor (22a), a baffle (24a), at least one inclined bore (26a) and a cap (28a). The turbine rotor (22a) is rotatably received in the pulsating engine (20a) and has a structure same as that of the turbine rotor (22) of the first embodiment as shown in FIG. 1. The baffle (24a) is formed at the entrance of the pulsating engine (20a) in the outlet end of the handle (10a) so as to define a chamber (14a) in the pulsating engine (20a). The cap (28a) is attached to the handle (10) to close the chamber (14a), and the cap (28a) has at least one through hole (282a) communicating with the chamber (14a). At least one inclined bore (26a) is defined through the baffle (24a) and communicates with the chamber (14a). In use, the sprayer can be connected to a water tap as the first embodiment.

Figure 8:
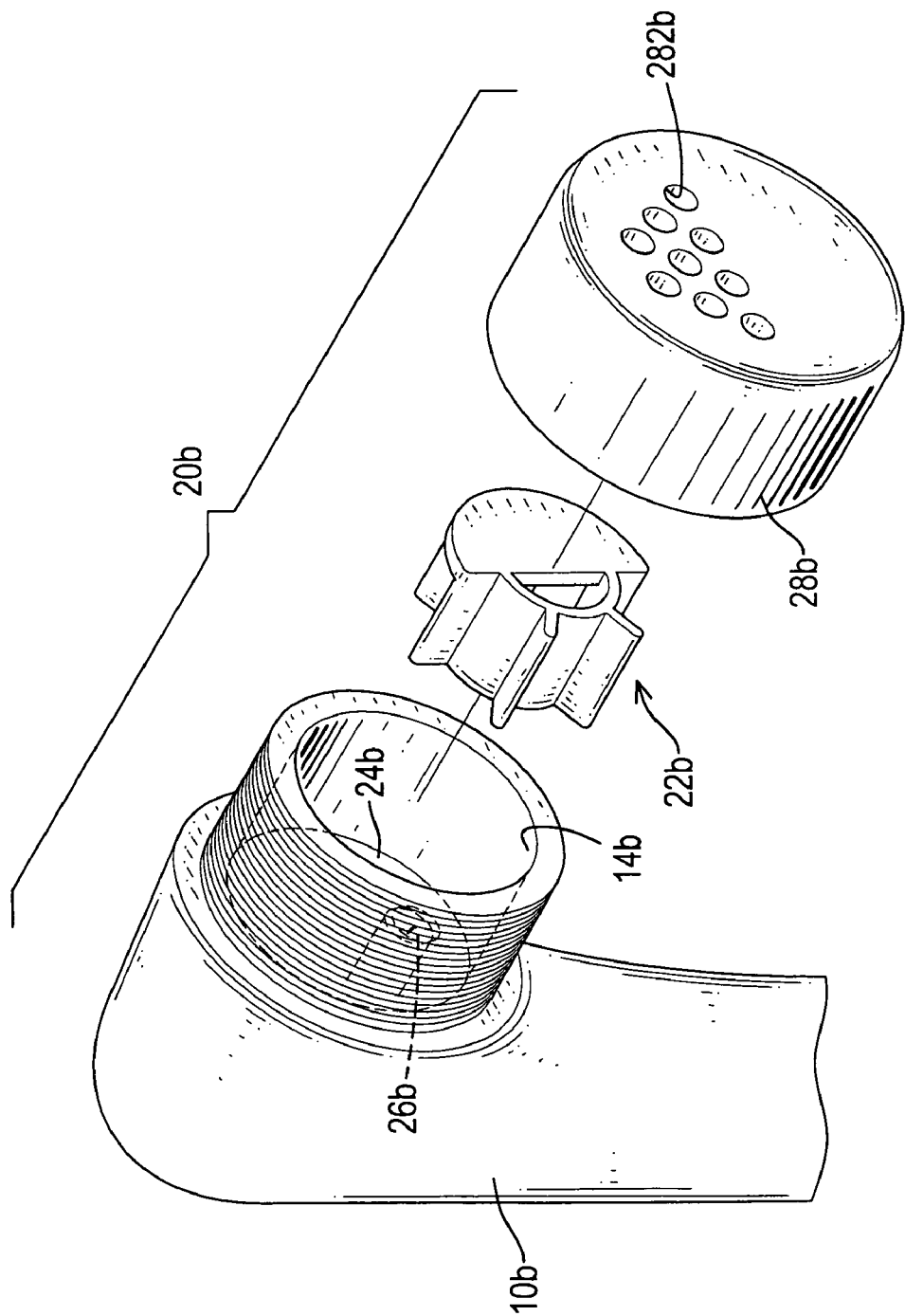
FIG. 8 is an exploded perspective view of a third embodiment of a sprayer in accordance with the present invention.
Figure 9:
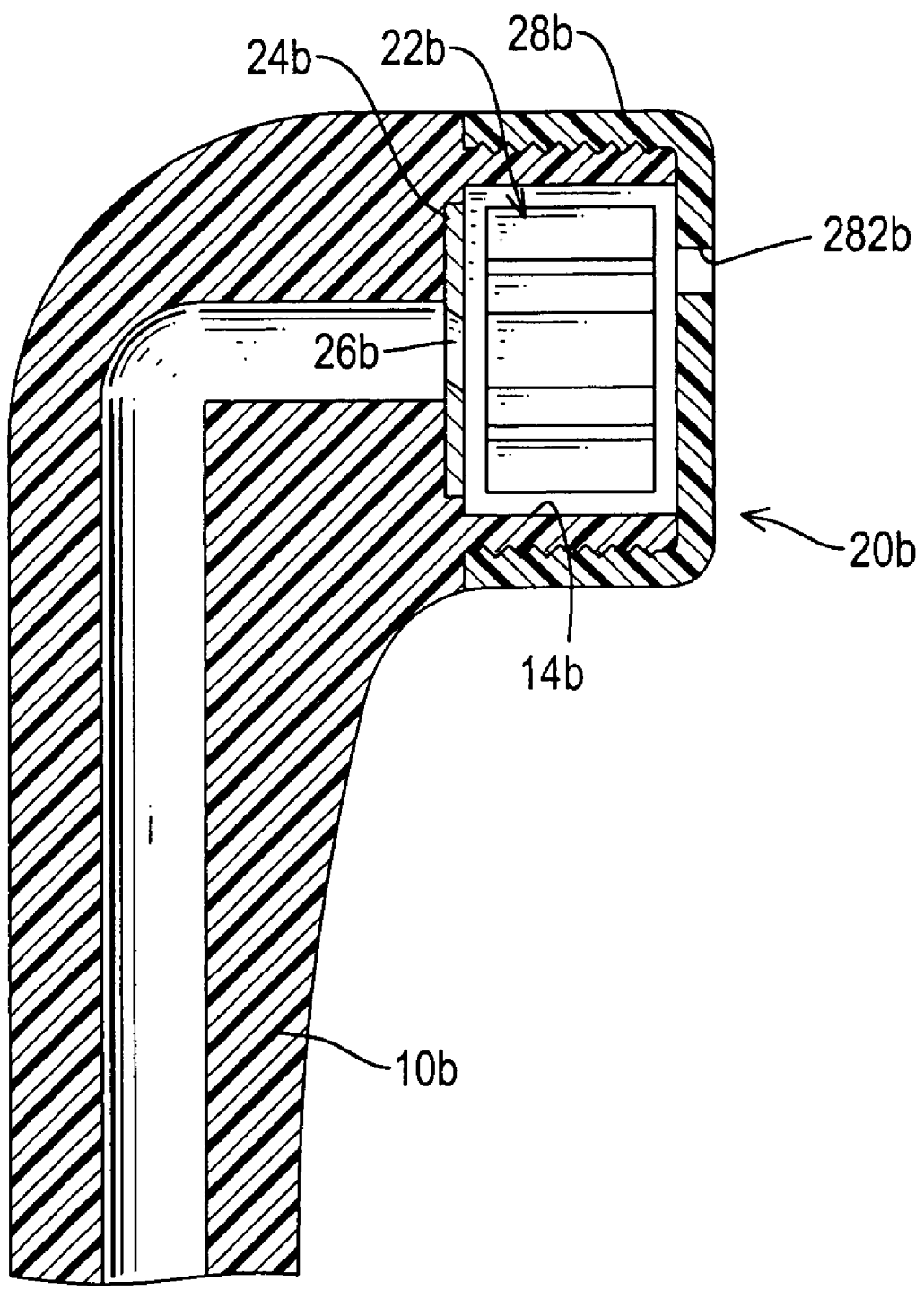
FIG. 9 is a side plan view in partial cross section of the sprayer in FIG. 8.

With reference to FIGS. 8 and 9, in a third embodiment of a sprayer in accordance with the present invention, the sprayer comprises a handle (10b) and a pulsating engine (20b). The handle (10b) has a L-shaped outlet end, an inlet end and a first passage and is connected to a water source through a hose. The pulsating engine (20b) is connected to the outlet end of the handle (10b) and has a turbine rotor (22b), a baffle (24b), at least one inclined bore (26b) and a cap (28b). The turbine rotor (22b) is rotatably received in the pulsating engine (20b) and has a structure same as that of the turbine rotor (22) of the first embodiment as shown in FIG. 1. The baffle (24b) is formed at the entrance of the pulsating engine (20b) in the outlet end of the handle (10b) so as to define a chamber (14b) in the pulsating engine (20b). The cap (28b) is attached to the handle (10b) to close the chamber (14b), and the cap (28b) has at least one through hole (282b) communicating with the chamber (14b). At least one inclined bore (26b) is defined through the baffle (24b) and communicates with the chamber (14b). In use, the sprayer can be connected to a water tap as the first embodiment.

When the user turns on the water tap, the water will flow into the chamber (14b) through at least one inclined bore (26b) and will spray out from the through holes (282b) in the cap (28b). When water passes through the chamber (14b), the water will impact on the blades of the turbine rotor (22b) so as to rotate the turbine rotor (22b) in the chamber (14b) so as to make a pulsating stream.

Figure 10:
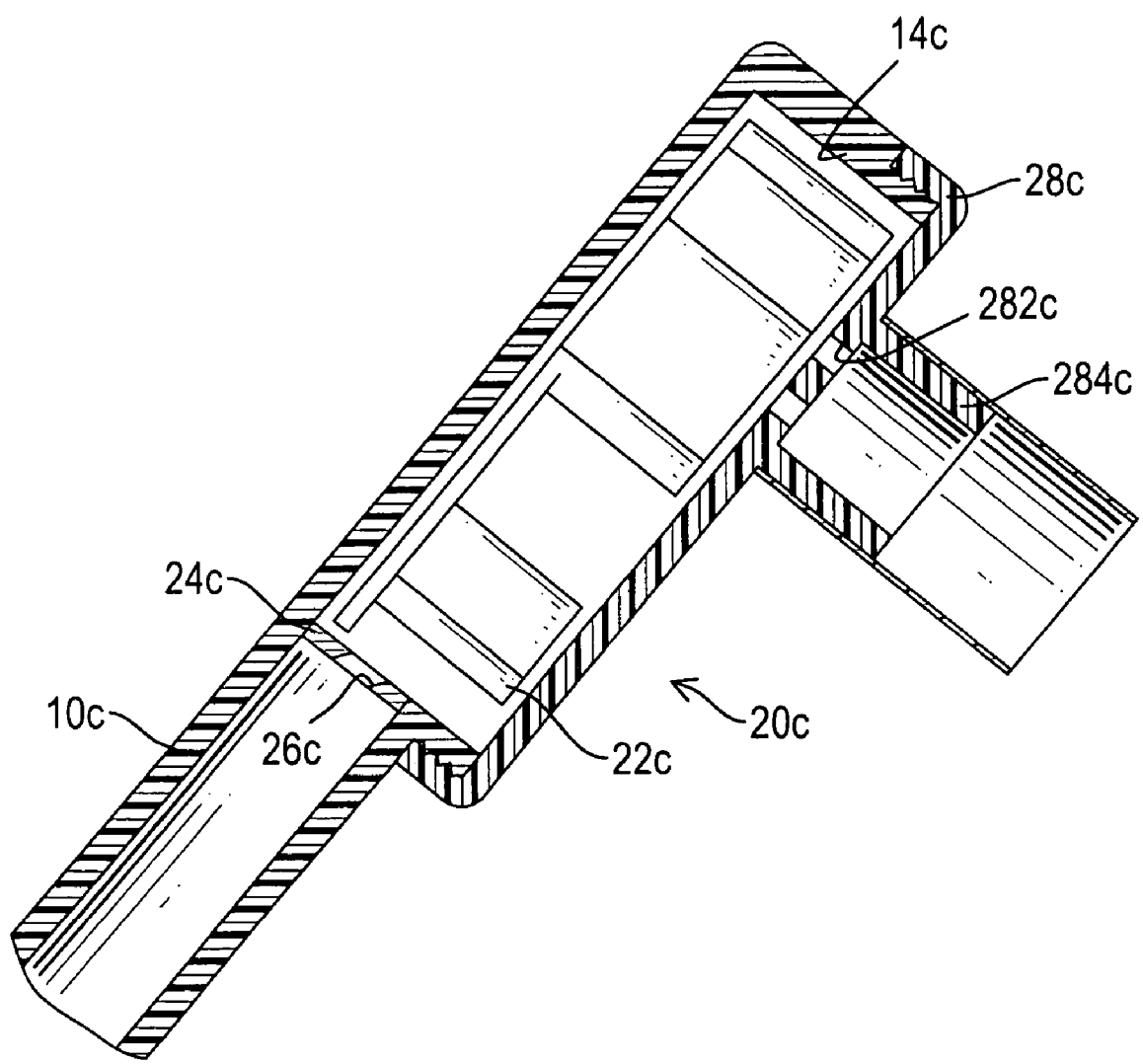
FIG. 10 is a side plan view in partial cross section of a fourth embodiment of a sprayer in accordance with the present invention.

With reference to FIG. 10, in a fourth embodiment of a sprayer in accordance with the present invention, the handle (10c) has a closed outlet end. The pulsating engine (20c) is connected to the outlet end of the handle (10c) and has a turbine rotor (22c), a baffle (24c), at least one inclined bore (26c) and a cap (28c). The turbine rotor (22c) is rotatably received in the pulsating engine (20c) and has a structure same as that of the turbine rotor (22) of the first embodiment as shown in FIG. 1. The baffle (24c) is formed at the entrance of the pulsating engine in outlet end the handle (10c) so as to define a chamber (14c) in the pulsating engine (20c). At least one inclined bore (26c) is defined through the baffle (24c) to communicate with the chamber (14c). The cap (28c) is attached to the handle (10c) to close the chamber (14c), and the cap (28c) has at least one through hole (282c) communicating with the chamber (14c) and a tube (284c). The tube (284c) extends from the cap (28c) and communicates with the through holes (282c).

Figure 11:
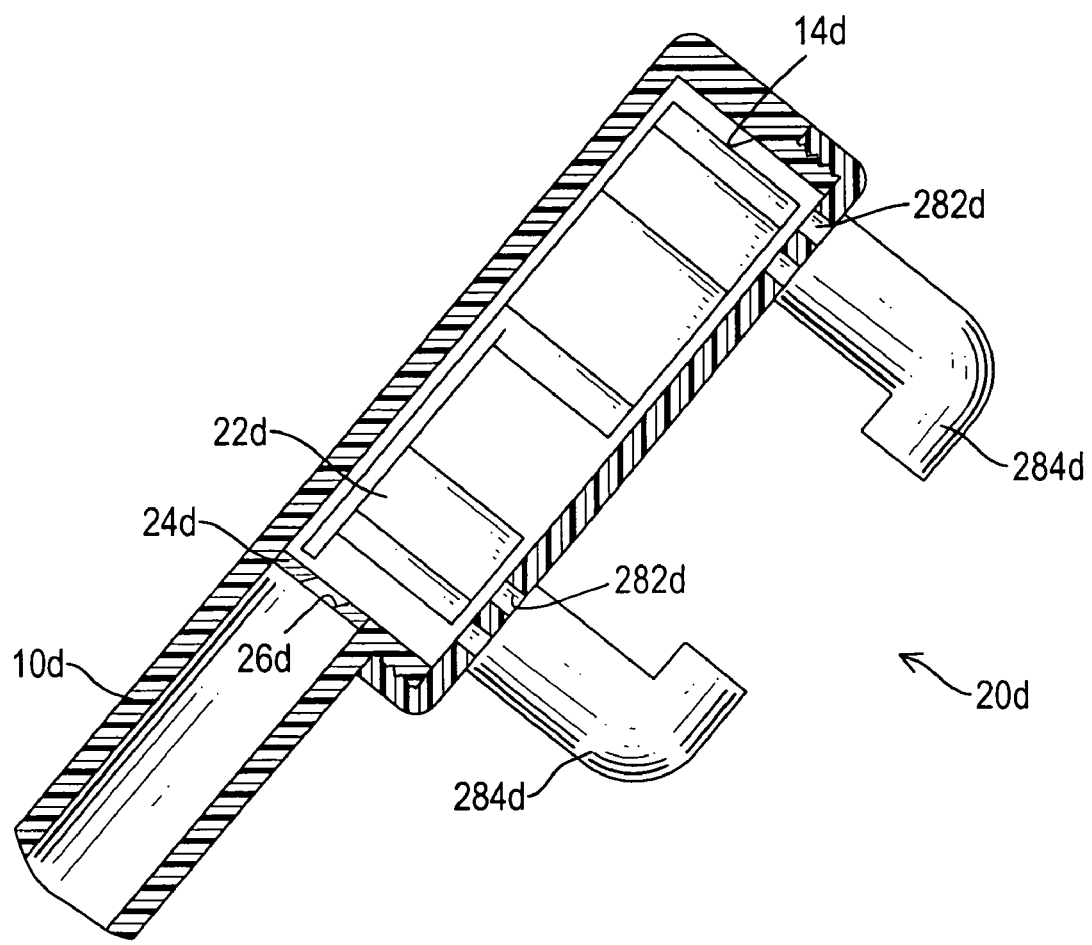
FIG. 11 is a side plan view in partial cross section of a fifth embodiment of a sprayer in accordance with the present invention.

With reference to FIG. 11, in a fifth embodiment of a sprayer in accordance with the present invention, the handle (10d) has a closed outlet end. The pulsating engine (20d) is connected to the outlet end of the handle (10c) and has a turbine rotor (22d), a baffle (24d), at least one inclined bore (26d) and a cap (28d). The turbine rotor (22d) is rotatably received in the pulsating engine (20d) and has a structure same as that of the turbine rotor (22) as shown in the first embodiment in FIG. 1. The baffle (24d) is formed at the entrance of the pulsating engine (20d) in the outlet end the handle (10d) so as to define a chamber (14d) in the pulsating engine (20d). At least one inclined bore (26d) is defined through the baffle (24d) to communicate with the chamber (14d). The cap (28d) is attached to the handle (10d) to close the chamber (14d) and has at least one through hole (282d) communicating with the chamber (14d) and two tubes (284d). The through holes (282d) are arranged on the opposite side of the circle respectively in two groups to deliver pulsating stream alternatively. The tubes (284d) are mounted on and extend from the cap (28d), and the tubes (284d) respectively communicate with the two groups of the through holes (282d). In a preferred embodiment, each tube (284d) is L-shaped and has an opening facing each other. Accordingly, the water spraying out from the openings of the tubes (284d) can conveniently clean both sides of teeth of the user.

Figure 12:
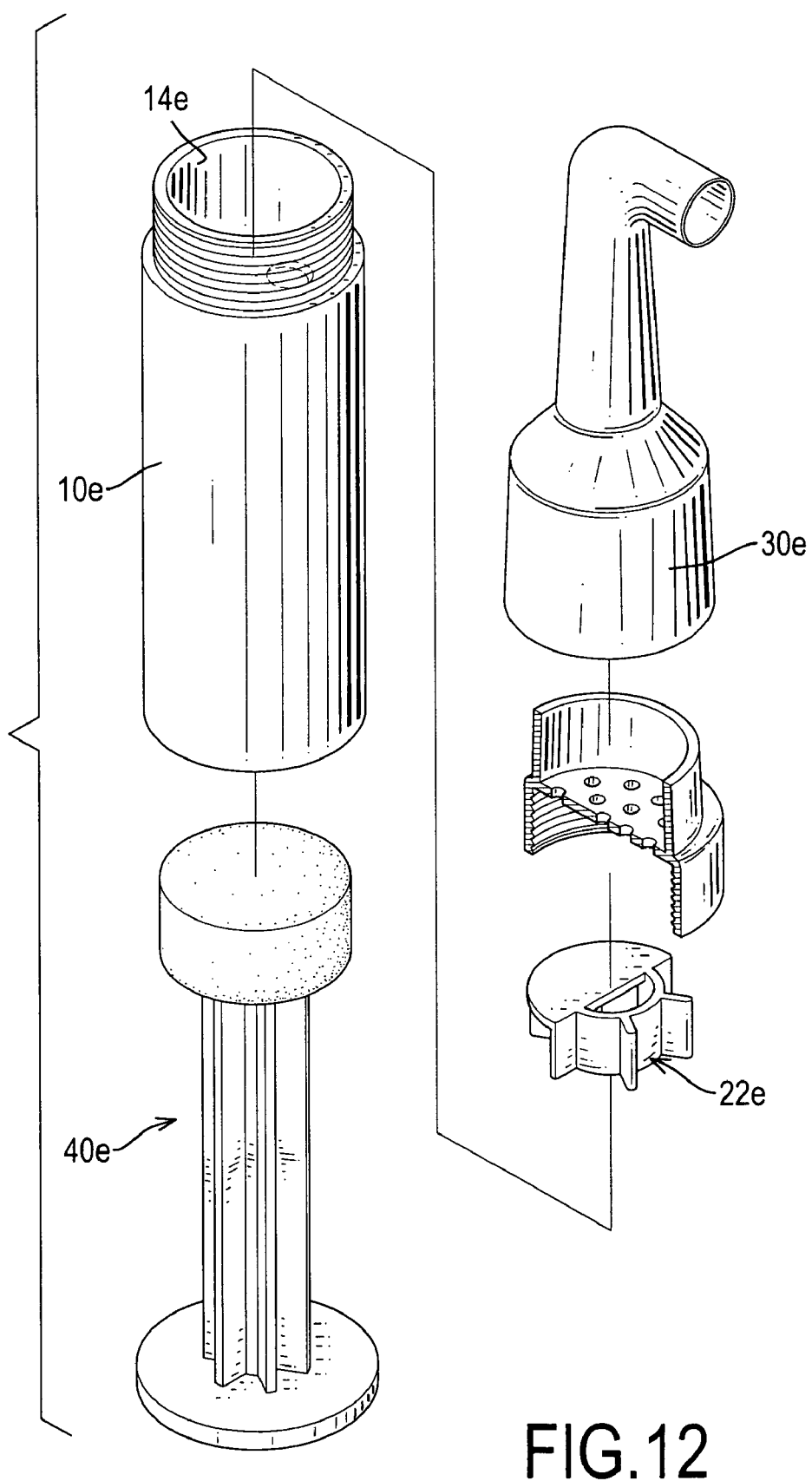
FIG. 12 is an exploded perspective view of a sixth embodiment of a sprayer in accordance with the present invention.
Figure 13:
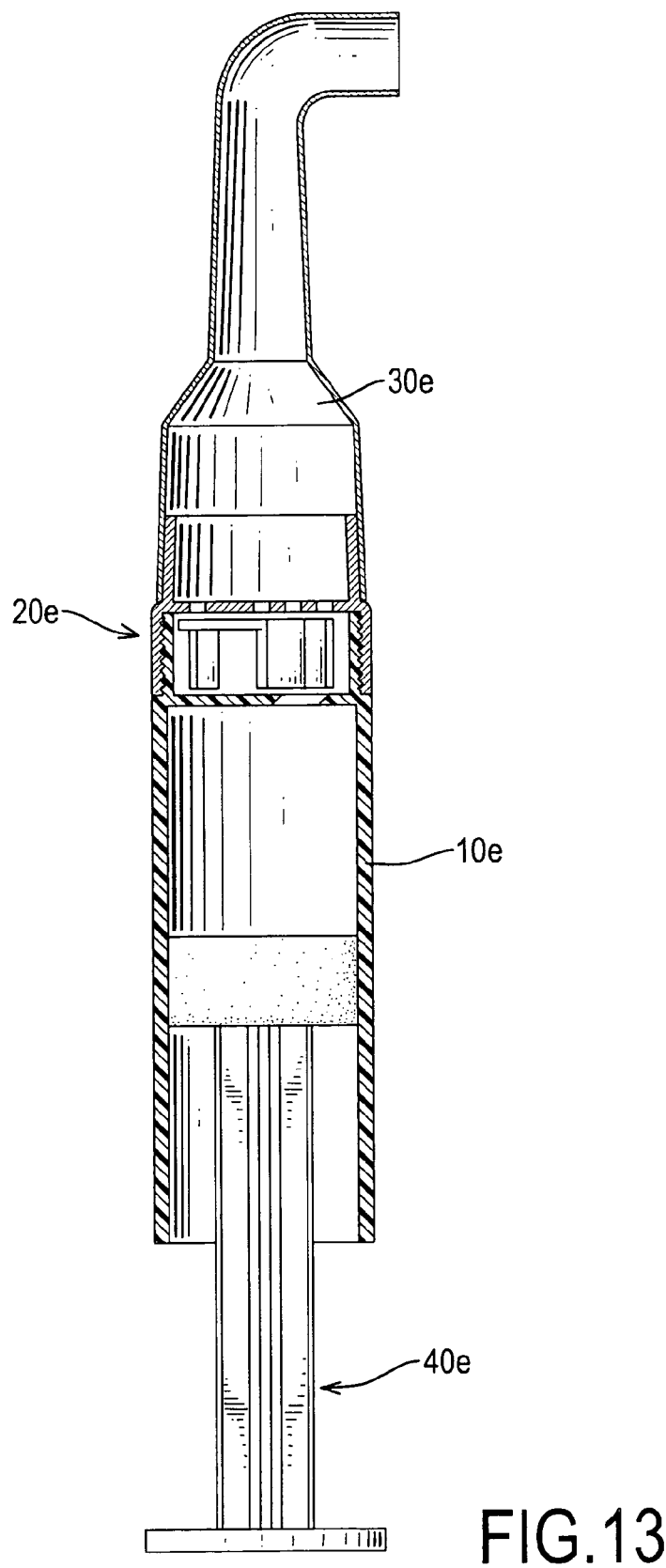
FIG. 13 is a side plan view in partial cross section of the sprayer in FIG. 12.

With reference to FIGS. 12 and 13, in a sixth embodiment of a sprayer in accordance with the present invention, the sprayer further comprises a plunger (40e). The plunger (40) is inserted into the handle (10e) from the inlet end of the handle (10e). In such an arrangement, water is poured into the passage in the handle (10e), and the plunger (40e) is inserted into the handle (10e). The water in the handle (10e) will be forced into the chamber (14e) to drive the turbine rotor (22e) rotation when the plunger (40e) is pushed into the handle (10e), and the water will discharge from the spraying head (30e) with a pulsating effect provided by the turbine rotor (22e). Thus, the device is portable and convenient for use away from home.

Figure 14:
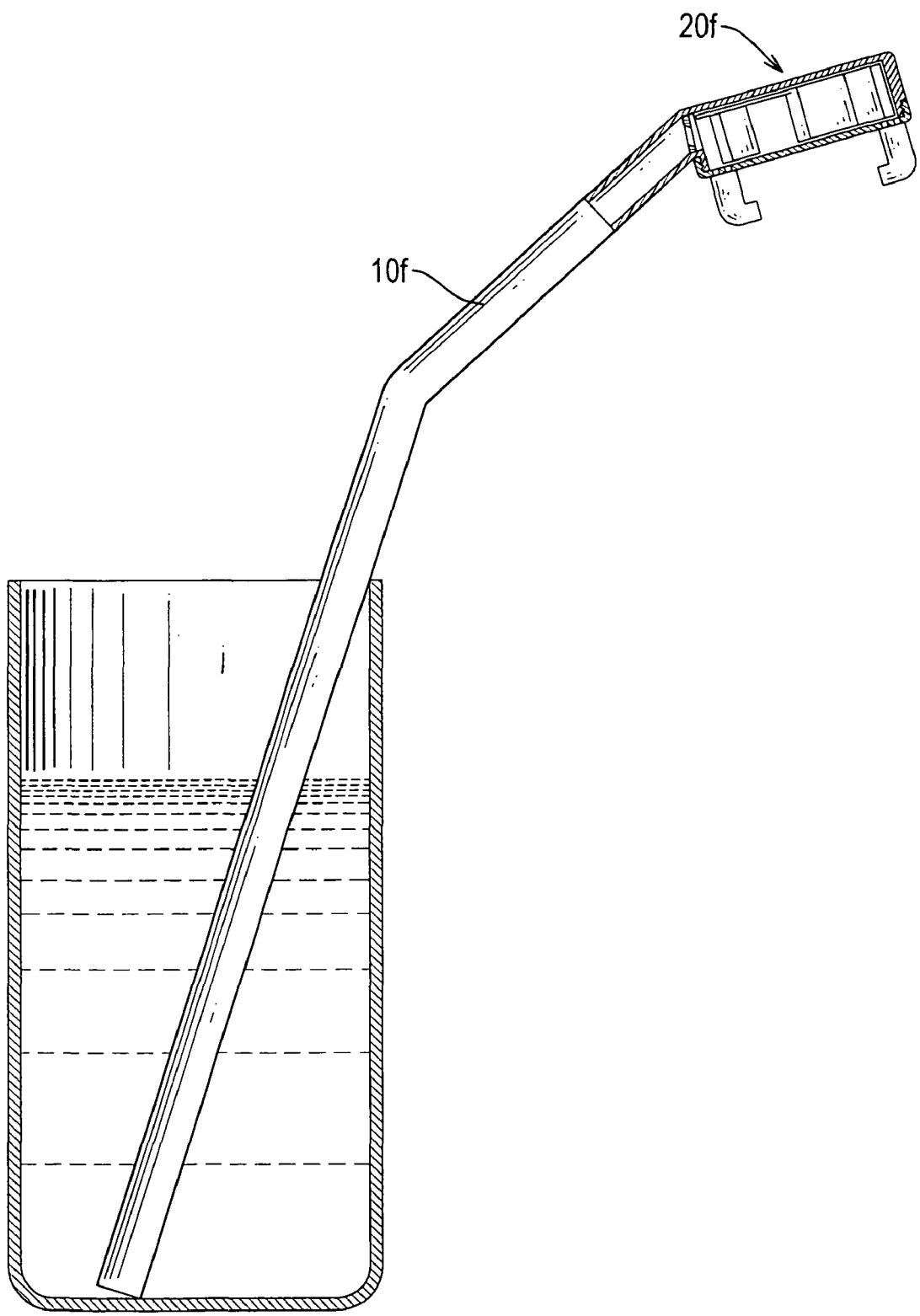
FIG. 14 is an operational side plan view in partial cross section of a seventh embodiment of a sprayer in accordance with the present invention.

With reference to FIG. 14, in a seventh embodiment of a sprayer in accordance with the present invention, the handle (10f) of the sprayer can be a tubular body formed as a sucking tube. In operation of the embodiment, the handle (10f) is put into a cup containing water. The user keeps the pulsating engine (20f) in mouth and sucks water through passage in the handle (10f). The pulsating stream will alternatively spray out from the tubes mounted on the cap of the pulsating engine (20f) for cleaning both sides of teeth of the user with a pulsating massage effect provided by the turbine rotor. Thus, the device is portable and convenient for use away from home.

Figure 15:
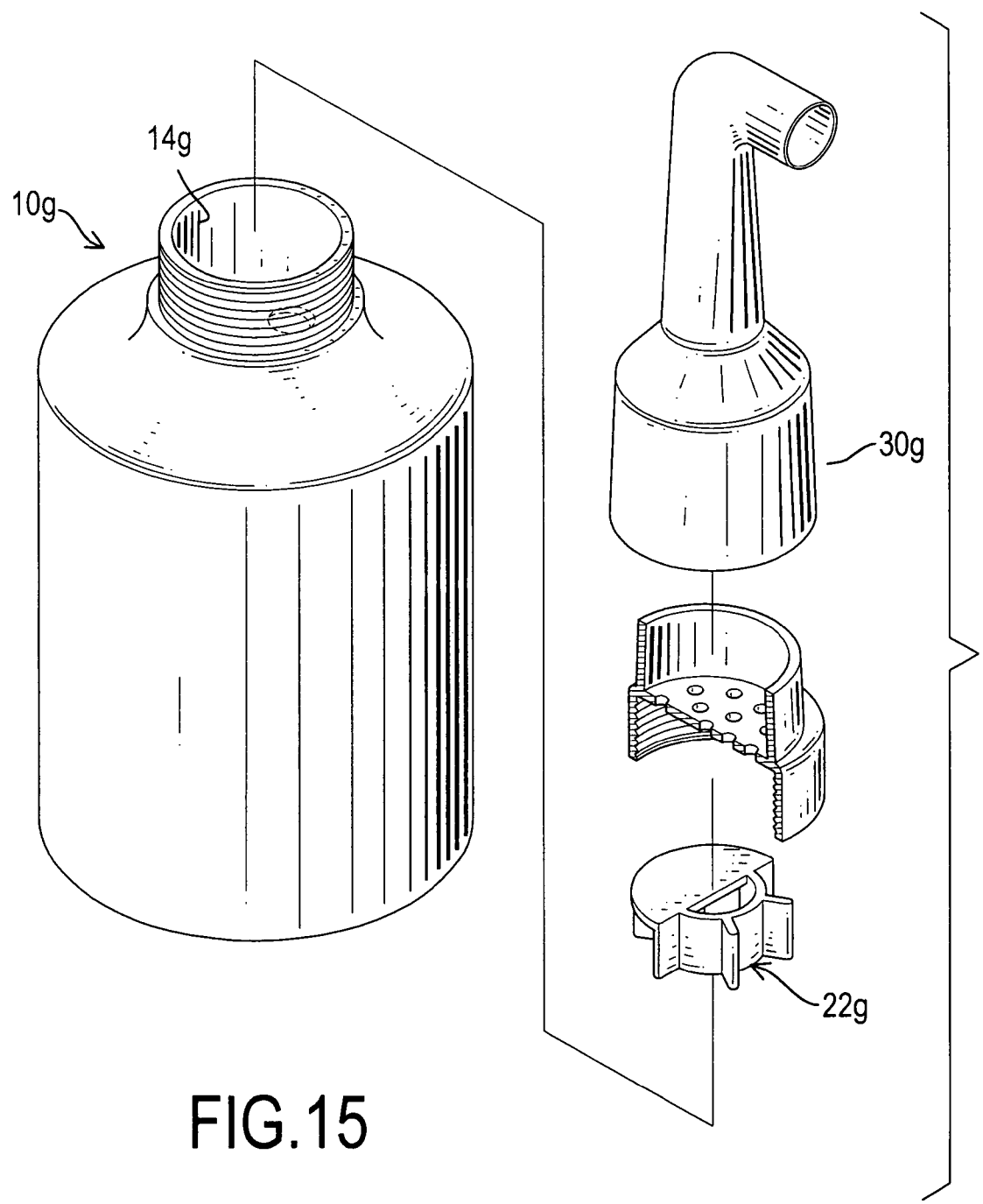
FIG. 15 is an exploded perspective view of an eighth embodiment of a sprayer in accordance with the present invention.

With reference to FIG. 15, in an eighth embodiment of a sprayer in accordance with the present invention, the handle (10g) of the sprayer can be a squeezing bag filled with water. In operation of the embodiment, the water in the handle (10g) will be forced into the chamber (14g) to drive the turbine rotor (22g) rotation when the user squeezes the handle (10g), and the water will discharge from the spraying head (30g) with a pulsating effect provided by the turbine rotor (22g). Thus, the device is portable and convenient for use away from home.

Figure 16:
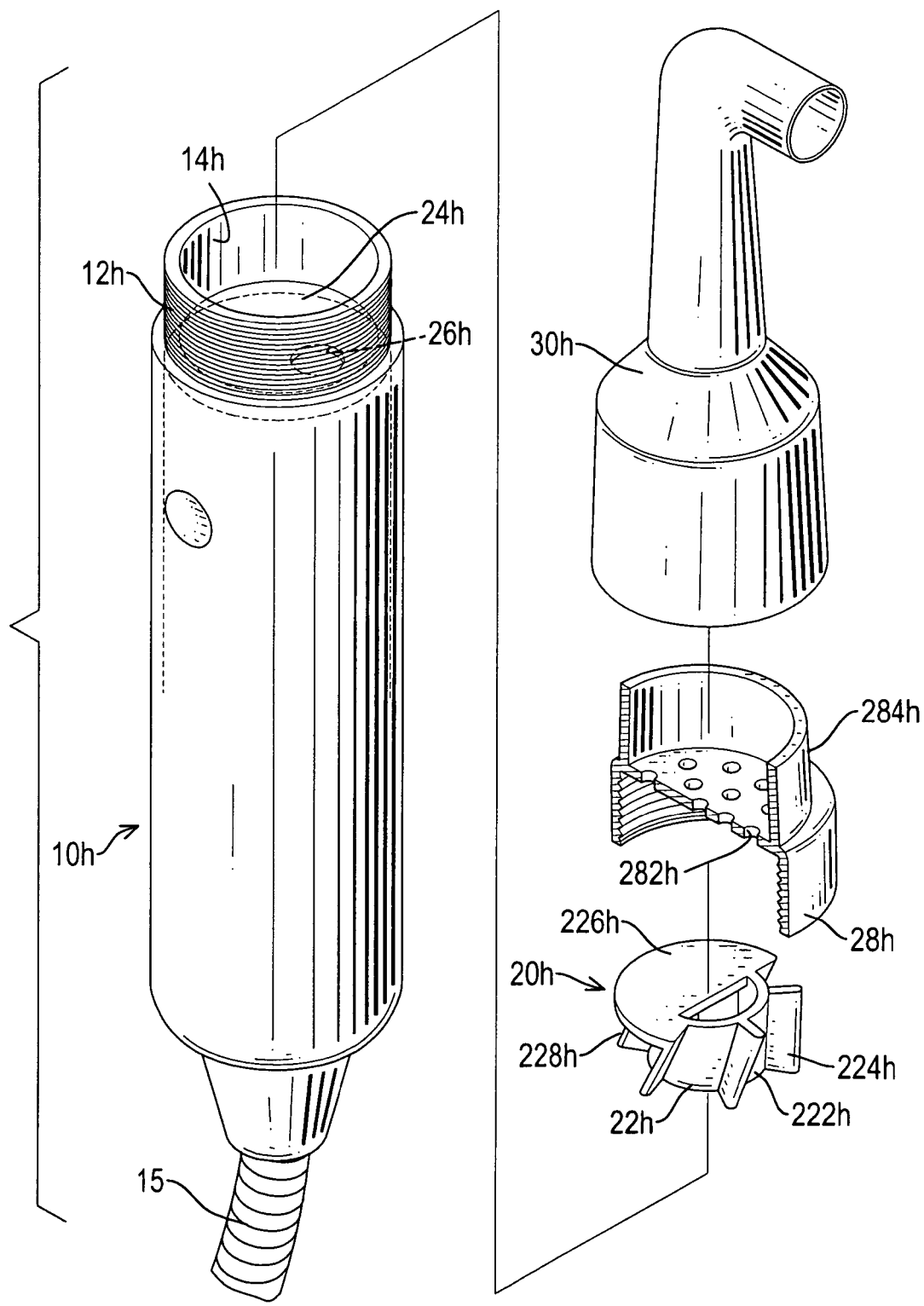
FIG. 16 is an exploded perspective view of a ninth embodiment of a sprayer in accordance with the present invention.

With reference to FIG. 16, in a ninth embodiment of a sprayer in accordance with the present invention, the pulsating engine (20h) has a turbine rotor (22h), a baffle (24h), at least one bore (26h) and a cap (28h). The turbine rotor (22h) is rotatably received in the pulsating engine (20h) and has a curved wall (222h), multiple first extension blades (224h), a top cover (226h) and multiple second extension blades (228h). The extension blades of the turbine rotor (22h) extend obliquely from the top cover (226h) and the outer periphery of the curved wall (222h) and are inclined toward the direction of water stream.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A pulsating dental sprayer comprising:
   a handle having an inlet end, an outlet end and a first passage defined through the handle;
   a pulsating engine connected to the outlet end of the handle and having a turbine rotor rotatably received in the pulsating engine and comprising
      a curved wall having an outer periphery;
      multiple first extension blades formed on and extending radially from the outer periphery of the curved wall;
      a top cover attached to the curved wall to construct a circle in cooperation with the curved wall; and
      multiple second extension blades radially formed on the top cover and corresponding to the first extension blades on the curved wall.

2. The dental sprayer as claimed in claim 1 further comprising a spraying head connected to the pulsating engine and having a second passage communicating with the pulsating engine.

3. The dental sprayer as claimed in claim 2, wherein the pulsating engine further comprises
   a baffle formed at an entrance of the pulsating engine in the outlet end of the handle to define a chamber in the pulsating engine connected to the outlet end of the handle;
   at least one inclined bore defined through the baffle and communicating with the chamber with the first passage; and
   a cap attached to the outlet end of the handle to close the chamber; and
   the turbine rotor is rotatably received in the chamber.

4. The dental sprayer as claimed in claim 3, wherein the cap further comprises
   at least one through hole defined in the cap and communicating with the chamber; and
   a connecting tube extending from the cap and enclosing the at least one through hole, wherein the spraying head is attached to the connecting tube on the cap.

5. The dental sprayer as claimed in claim 4, wherein the cap of the pulsating engine is mounted with the outlet end of the handle to close the chamber in a threaded manner.

6. The dental sprayer as claimed in claim 5, wherein a ratio of the top cover to the circle constructed by the top cover in cooperation with the curved wall is equal to ratio of total distributed area of the at least one through hole to area of the cap.

7. The dental sprayer as claimed in claim 6, wherein the at least one through hole is arranged within a portion of the cap that is fully coverable by the top cover.

8. The dental sprayer as claimed in claim 7 further comprising a plunger inserted into the handle at the inlet end.

9. The dental sprayer as claimed in claim 2, wherein the spraying head is L-shaped.

10. The dental sprayer as claimed in claim 1, wherein the pulsating engine further comprises
    a baffle formed at an entrance of the pulsating engine in the outlet end of the handle so as to define a chamber in the pulsating engine connected to the outlet end of the handle;
    at least one inclined bore defined through the baffle and communicating the chamber with the first passage; and
    a cap attached to the outlet end of the handle to close the chamber; and
    the turbine rotor is rotatably received in the chamber.

11. The dental sprayer as claimed in claim 10, wherein the cap further comprises
   at least one through hole defined in the cap and communicating with the chamber; and
   a tube extending from the cap and communicating with the at least one through hole.

12. The dental sprayer as claimed in claim 10, wherein the cap further comprises
   multiple through holes defined in the cap and arranged on the opposite side of the circle respectively in two groups to deliver pulsating stream alternatively; and
   two tubes extending from the cap and respectively communicating with the two groups of the through holes.

13. The dental sprayer as claimed in claim 12, wherein each respective tube is L-shaped and has an opening facing to each other.

14. The dental sprayer as claimed in claim 13, wherein the handle is a tubular body formed as a sucking tube.

15. The dental sprayer as claimed in claim 7, wherein the handle is a squeezing bag.

16. The dental sprayer as claimed in claim 1, wherein the extension blades are inclined toward a direction of water stream.

17. The dental sprayer as claimed in claim 5, wherein a ratio of the top cover to the circle constructed by the top cover in cooperation with the curved wall is greater than the ratio of total distributed area of the at least one through hole to area of the cap.

* * * * *